United States Patent [19]

Bradley

[11] 4,201,212

[45] May 6, 1980

[54] SURGICAL APPARATUS FOR USE IN SYRINGING A PATIENT'S EAR

[76] Inventor: Margaret E. Bradley, Fairholme, Higher Hill, Tockholes, Near Darwen, Lancashire, England

[21] Appl. No.: 888,366

[22] Filed: Mar. 20, 1978

[30] Foreign Application Priority Data

Mar. 24, 1977 [GB] United Kingdom ............... 12368/77

[51] Int. Cl.² .............................................. A61F 5/44
[52] U.S. Cl. .................................... 128/275; 128/760; 128/292
[58] Field of Search ................... 128/275, 2 F, 132 R, 128/141, 292; 4/113, 144.1, 144.2, 144.3, 144.4, 274; 222/175; 141/340

[56] References Cited

U.S. PATENT DOCUMENTS

| | | | |
|---|---|---|---|
| 1,208,139 | 12/1916 | Graham | 128/248 |
| 1,500,927 | 7/1924 | Davies et al. | 128/275 |
| 3,585,997 | 6/1971 | Ancerewicz, Jr. | 128/275 |
| 3,661,143 | 5/1972 | Henkin | 128/2 F |
| 4,036,235 | 7/1977 | Hathaway | 128/292 |

Primary Examiner—Robert W. Michell
Assistant Examiner—J. Kruter
Attorney, Agent, or Firm—Norris & Bateman

[57] ABSTRACT

Surgical apparatus for use in the syringing of a patient's ear comprising a receptacle having an upwardly extending wall shaped to fit the side of the patient's head the wall having a first downwardly extending recess to receive the ear to be syringed with the portions of the wall on either side of the recess extending upwardly, in front of and behind the ear, the wall having a second downwardly extending recess opposite the said first recess, through which a syringe can be inserted to pass across the receptacle and into the ear, and fastening means to hold the receptacle in position on the patient's head and urge the wall of the receptacle into sealing engagement with the side of the patient's head.

8 Claims, 4 Drawing Figures

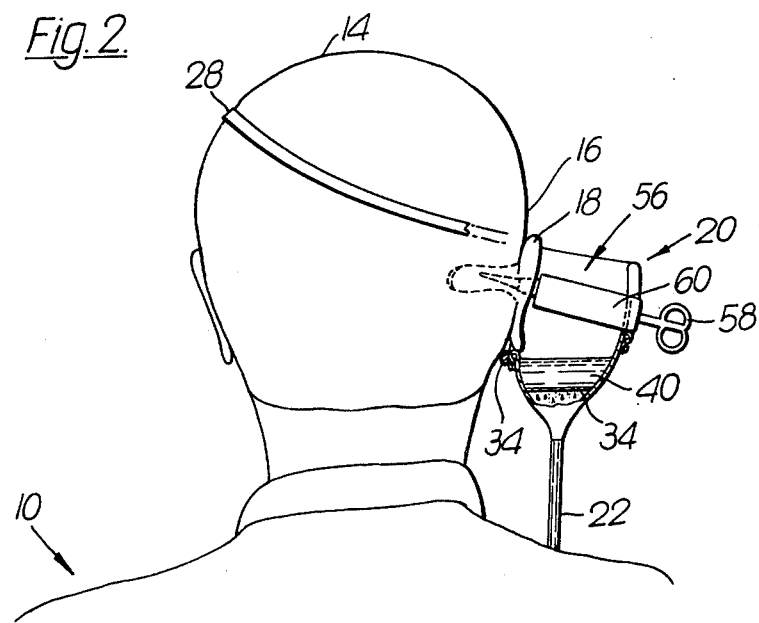
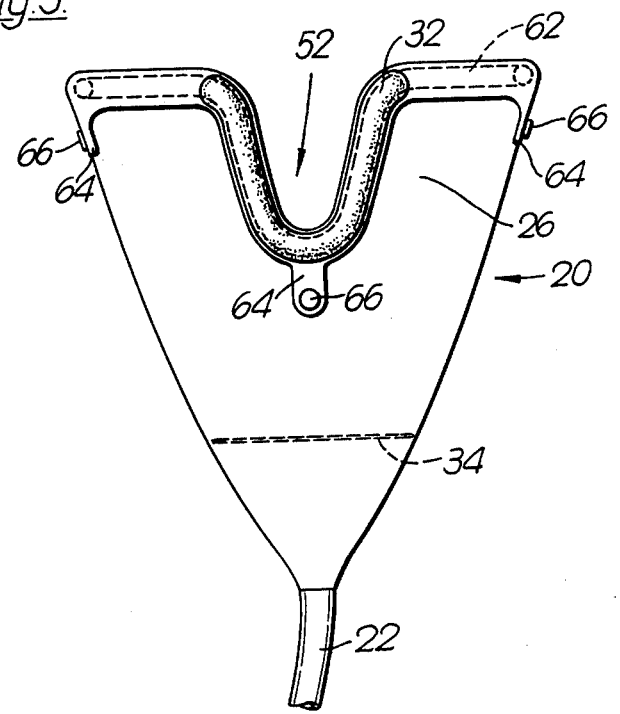

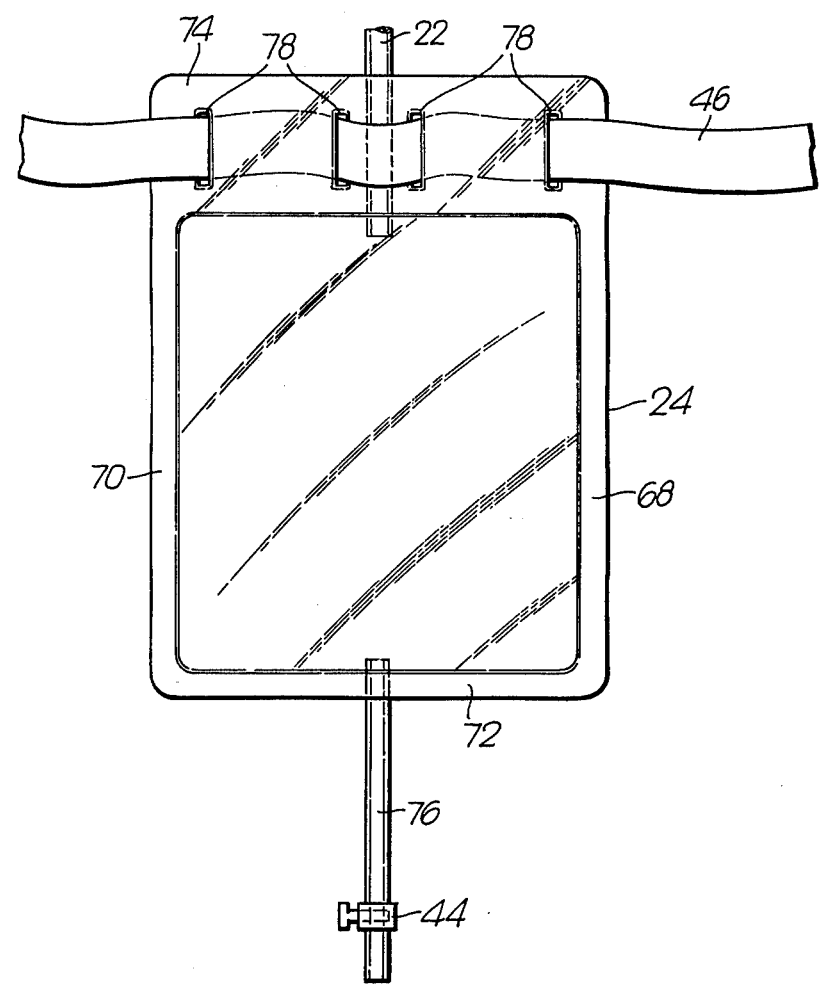

SURGICAL APPARATUS FOR USE IN SYRINGING A PATIENT'S EAR

BACKGROUND TO THE INVENTION

The invention relates to surgical apparatus and more particularly to apparatus for use in the syringing of a patient's auditory passage.

DESCRIPTION OF THE PRIOR ART

When a patient's ear becomes infected or is blocked by an accumulation of wax therein, it is a usual surgical practice to apply a cleansing or sluicing fluid to the outermost ear passage by means of a syringe inserted within that passage. The fluid is caused to circulate within the passage by the pressure applied to the fluid by the syringe and the fluid then drains out from the ear, carrying with it wax or other foreign matter from the ear. The fluid, wax or other foreign matter draining from the ear is collected in a dish or other vessel which is held against the patients's head below the ear which is being syringed. Normally at least one to two pints of fluid are used to syringe the ear and the dish or other vessel consequently needs to be emptied to prevent fluid spilling over the edge thereof as the syringing of the ear takes place. The syringing process is thus intermittent and the person, most usually a nurse, performing the syringing process has to empty the dish or other vessel periodically as it becomes full of fluid.

Where a patient, such as a young child, or an elderly person, is incapable of holding the dish or other vessel at the required position below the ear during the syringing of an ear, a second nurse may be needed to hold the dish or other vessel in position while the first nurse performs the syringing process. It would be advantageous if the second nurse did not have to be involved in the syringing process at all since that nurse could then carry out other more pressing medical duties. It often happens, even with a second nurse or with a patient who is capable of holding the dish or vessel at the required position, that there is spillage of the fluid from the dish or other vessel. This makes the syringing process messy and uncomfortable for the patient, especially when that patient is involved in holding the dish or other vessel during the syringing of their own ear.

In spite of the many inconveniences of the present method of merely having the patient hold a dish underneath their own ear, no-one has yet developed a satisfactory alternative. It is known, when carrying out a test of vestibular function, known as the caloric test, to hang a small funnel below the ear of a patient, suspending the funnel from a chain looped over the patient's ear, in order to collect the large volumes of water used in the caloric test. However I consider that the use of such a known funnel would be quite unsuitable for the different technique of syringing. In the syringing process, liquid is squirted into the ear from a syringe. The liquid is therefore under pressure and tends to spray back out of the ear. This spray would not be collected in the conventional funnel used in the caloric test and furthermore liquid would leak down the side of the patient's face between the face and the funnel, causing discomfort to the patient.

OBJECTS OF THE INVENTION

It is an object of the invention to provide surgical apparatus which greatly facilitates the technique of ear syringing.

It is an additional object of the invention to provide surgical apparatus which enables ear syringing to be carried out with less inconvenience and discomfort to the patient.

It is a further object of the invention to provide surgical apparatus for use in ear syringing which facilitates the examination of any foreign matter dislodged from the ear.

It is a still further object of the invention to provide surgical apparatus for use in ear syringing which can be manufactured simply and cheaply.

It is yet another object of the invention to provide surgical apparatus which can be used not only for ear syringing but also for carrying out the caloric test of vestibular function.

SUMMARY OF THE INVENTION

The invention provides surgical apparatus for use in the syringing of a patient's ear, comprising a receptacle having an upwardly extending wall shaped to fit the side of the patient's head, the wall having a first downwardly extending recess to receive the ear to be syringed, with the portions of the wall on either side of the recess extending upwardly, in front of and behind the ear, the wall having a second downwardly extending recess opposite the said first recess, through which a syringe can be inserted to pass across the receptacle and into the ear, and fastening means to hold the receptacle in position on the patient's head and urge the wall of the receptacle into sealing engagement with the side of the patient's head.

With the apparatus according to the invention, there is no need for the patient or a nurse to hold the receptacle in position. The fastening means hold the receptacle securely in position and since it also urges the wall of the receptacle against the side of the patient's head, the leakage of liquid down the side of the patient's head is minimised. Sinc the ear fits into one recess in the receptacle and the syringe is inserted through another recess opposite the first recess, the upper parts of the wall of the receptacle form a shield which catches substantially all the liquid spraying back out of the ear and directs it into the bottom of the receptacle.

Preferably the fastening means comprises an elastic strap which can be fastened about the patient's head, since this provides a simple and convenient means whereby the receptacle can be held in position, the receptacle also being urged into sealing engagement with the patient's head. The elastic strap may be adjustable in length.

As an alternative one or more other adjustable straps or loops connected to the receptacle may be used as the fastening means.

I have found that a particularly cheap and effective way of manufacturing the receptacle is to manufacture a rigid frame member defining the upper extremities of the wall of the receptacle, and suspend a flexible bag from the rigid frame member. It is preferred that the flexible bag be releasably connected to the frame member so that the bag can not only be readily removed for cleaning or sterilisation purposes, but when the bag has completed its useful life, it can be disposed of and a fresh bag can be fitted to the rigid frame member.

To improve the seal against the patient's head, and also make the apparatus more comfortable to wear, a pad of resilient material is preferably arranged around the said first recess. A foam plastic material may for example be used.

Preferably the receptacle is provided with a drain tube which, when the apparatus is in use, can be used to conduct fluid from the receptacle to a drain or to a reservoir if it is desired to retain the fluid for examination.

To facilitate examination of wax or other foreign matter carried out of the ear by the liquid, the receptacle is preferably provided with a filter arranged to separate the foreign matter from the syringing liquid, as the syringing liquid passes out of the drain tube. The filter may comprise a perforated plate or sheet secured to the inner periphery of the receptacle at the base thereof.

The apparatus may include a reservoir (e.g. in the form of a flexible bag), the drain tube being connected or connectable to the bag to allow the syringing liquid to pass into the bag. The reservoir may have an outlet tap by means of which the syringing fluid can be emptied from the bag.

The apparatus may also comprise means to mount the reservoir on a support surface, for example the back of a chair on which the patient is seated.

The apparatus may comprise a first flexible plastic bag comprising the receptacle, a second flexible plastic bag comprising the reservoir, and a length of plastics tube welded between the two bags to provide a drain tube for conducting liquid from the receptacle to the reservoir. It is preferred that the drain tube, while being flexible, is also substantially resistant to transverse deformation so that the drain tube is less likely to become pinched when in use, thereby effectively blocking the tube and preventing passage of syringing fluid therethrough.

Further objects, features and advantages of apparatus according to the invention will become apparent from the following description of an embodiment of the invention.

BRIEF DESCRIPTION OF THE DRAWINGS

FIG. 2 is a diagrammatic rear view of part of the patient and apparatus shown in FIG. 1;

FIG. 3 is a view of the receptacle of the apparatus to a larger scale; and

FIG. 4 is a view of the reservoir to a larger scale.

DESCRIPTION OF AN EMBODIMENT OF THE INVENTION

Figure 1:
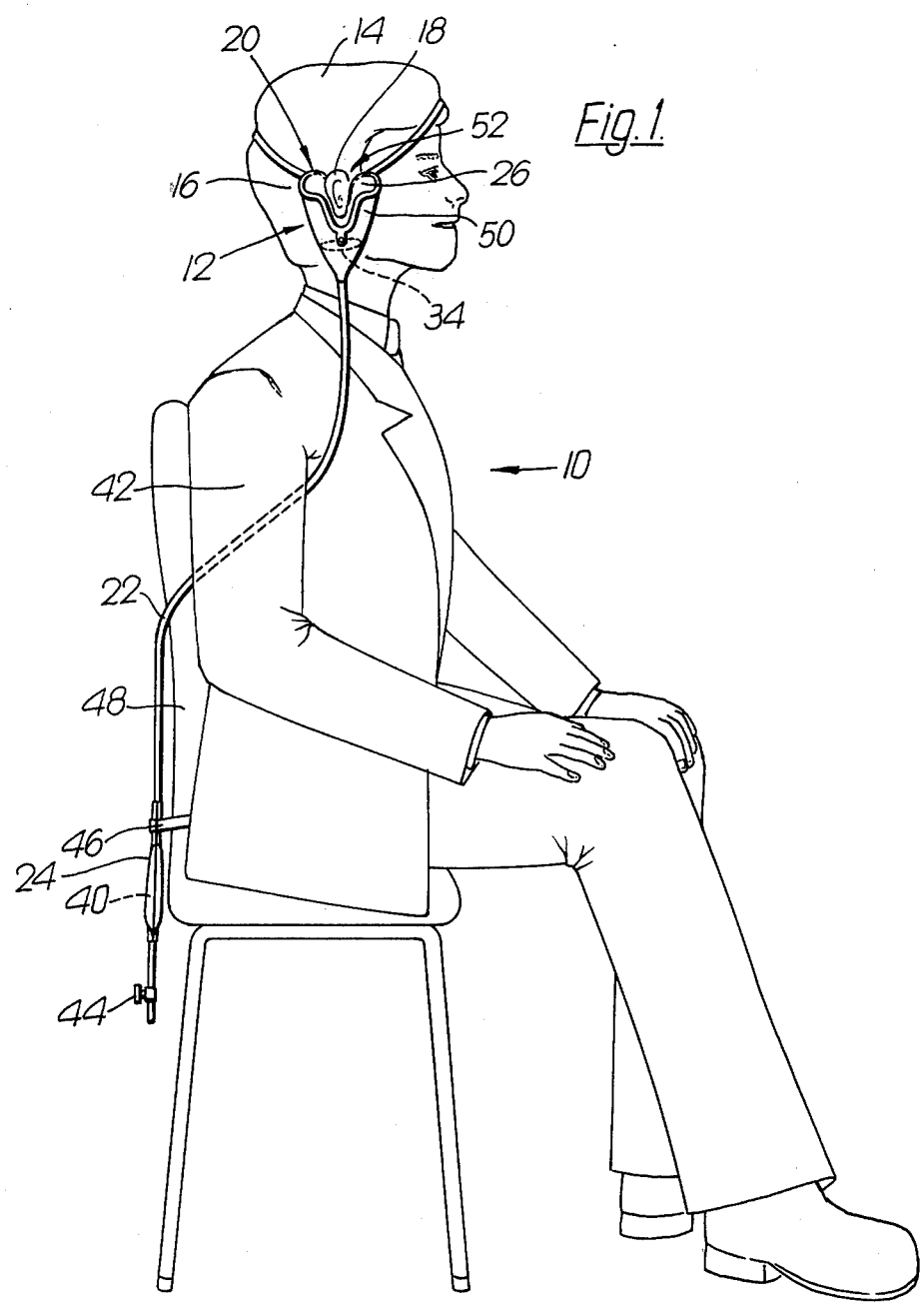
FIG. 1 is a diagrammatic side elevation of a patient seated on a chair, the patient having attached to his head an embodiment of apparatus according to the invention for use in the syringing of his ear.

A patient is indicated at 10 and a syringing apparatus indicated generally by reference numeral 12 is attached to the patient's head 14, the apparatus 12 being located on one side 16 of the patient's head 14 around an ear 18 to be syringed. The syringing apparatus comprises a substantially plastic receptacle 20 having a plastics drain tube 22 connected to the base thereof, and a plastics reservoir or collecting bag 24 connected via the tube 22 to the receptacle 20. At one side 26 of the receptacle there is connected an adjustable elasticated strap 28, which strap can readily be looped around the patient's head as best shown in FIG. 2, so that the side 26 of the receptacle 20 is urged against the side 16 of the patient's head 14. The receptacle 20 is made substantially of flexible plastics material and so the side 26 moulds itself to conform to the contours of the patient's head around the ear. The ear is received within a first downwardly extending recess 52 in the side 26 of the receptacle. A foam pad 32 is attached to the outer edge of the side 26 around the first recess 52 where it is arranged to engage the side 16 of the head 14 in order that the apparatus 12 is comfortably positioned on the patient 10 and does not irritate the skin on the side 16 of the head 14. The foam pad 32 also acts as a seal to restrict or prevent seepage of liquid between the receptacle 20 and the side 16 of the head 14.

A perforated sheet 34 is connected to the inner periphery of the base of the receptacle to form a filter which separates any foreign matter or wax from a syringing fluid 40 which is used to syringe the ear 18.

The drain tube 22 passes under the arm 42 of the patient 10 and is arranged to conduct the syringing fluid 40 from the receptacle 20 to the bag 24. The bag 24 has a tap 44 on the base thereof in order that the syringing fluid 40 can be drained from the bag after use. An adjustable strap 46 secures the bag to the rear of a chair 48 on which the patient 10 is seated, the weight of the bag 24 and the fluid 40 contained therein being supported by the strap.

The side 50 of the receptacle 20 which is opposite to the side 26 thereof has a rim which is slightly lower than the rim of the side 26 as seen in FIG. 2 and a second recess 52 is provided on the side 50. A syringe 56 can be inserted through the second recess to extend across the receptacle and into the ear as shown diagrammatically in FIG. 2.

Once the apparatus 12 is arranged on the patient as previously described, the syringe 56 containing the fluid 40 is inserted at an upwardly inclined angle into the ear 18 as shown in FIG. 2. A plunger 58 of the syringe is then forced into a barrel 60 of the syringe and the fluid 40 is thereby caused to circulate within the ear 18. The fluid 40 sprays back out of the ear and drains from the ear into the receptacle 20. The filter 36 separates any foreign matter and the fluid then passes on down the tube 22 to the bag 24.

Once the syringing process is complete, the apparatus is removed from the patient by slipping the elastic strap 28 off the head 14. The fluid 40 can then be removed from the bag 24 to waste by opening the tap 44. Any foreign matter retained on the filter 36 can be transferred to a laboratory for drying, examination and/or analysis.

It will be appreciated that since the apparatus 12 is connected to the patient 10, the patient is not required to take part in the syringing process and by providing a receptacle which seals against the side of the patient's head substantially all of the syringing fluid is caught by the receptacle and does not drain on to the patient. Also, since the bag 24 can be made with a capacity larger than two pints, the bag need not be emptied during the syringing process. The entire syringing process can be carried out without interruption and the bag need only be emptied after the process is complete and the apparatus has been removed from the patient.

By use of the apparatus the syringing process can be performed by one person without the assistance of the patient. The process can be carried out rapidly and is relatively comfortable for the patient.

Turning now to FIGS. 3 and 4, the construction of the receptacle 20 and the bag 24 will be described in more detail.

The receptacle 20 comprises a downwardly tapering flexible plastic bag suspended from a metal frame member 62. The shape of the metal frame member 62 defines the shape of the rim of the receptacle, the frame member having two downwardly extending loop portions to define the recesses 52. The metal frame member 62 is coated with plastics or other material to reduce corrosion and improve the appearance of the frame member. The tapering flexible plastic bag is secured to the frame member by folding the lip of the bag over the frame member and releasably securing the lip of the bag in the folded-over position by means of a plurality of tabs 64 which can be secured to the outer wall of the bag by press-studs 66.

To prevent liquid from spilling out through the recesses 52, the distance between the bottom of the recesses 52 and the filter 34 is preferbly at least two and a half inches.

The upper end of the drain tube 22 is secured to the bottom of the receptacle by a plastic welding technique.

As shown in FIG. 4, the reservoir bag 24 is formed by welding together two generally rectangular sheets of flexible plastics material around their edges 68, 70, 72, and 74. The lower end of the drain tube 22 is trapped between the edges 74 and welded thereto. Similarly a short flexible plastic outlet pipe 76 is trapped between the edges 72 and welded thereto. The pipe 76 carries the tap 44.

The welded portion of the edges 74 is considerably wider than the welded portion of the other edges, and in this wider welded portion four slits 78 are provided through which the adjustable plastics strap 46 is threaded.

The invention is not restricted to the details of the foregoing embodiment. For example the filter 34 may be arranged at an angle to the horizontal. The plastic bags and other plastic items may be of PVC, but the portion 74 of the bag 24, which carries the strap 46, may if desired be made of a different plastics material from the rest of the bag 24, and be welded thereto. The strap 46 may be permanently welded to the bag 24.

I claim:

1. Surgical apparatus for use in the syringing of a patient's ear, comprising a receptacle having an upwardly extending wall shaped to fit the side of the patient's head, the wall having a first downwardly extending recess to receive the ear to be syringed with the portions of the wall on either side of the recess extending upwardly, in front of and behind the ear, the wall having a second downwardly extending recess opposite the said first recess, through which a syringe can be inserted to pass across the receptacle and into the ear, and fastening means to hold the receptacle in position on the patient's head and urge the wall of the receptacle into sealing engagement with the side of the patient's head, the receptacle comprising a rigid frame member defining the upper extremities of the wall of the receptacle, and a flexible bag releasably connected to the frame member in such a manner that the flexible bag is suspended from the frame member.

2. Surgical apparatus as claimed in claim 1, in which the said fastening means comprises an elastic strap which can be fastened about the patient's head.

3. Surgical apparatus as claimed in claim 1, in which the wall of the receptacle has a pad of resilient material arranged around the said first recess to provide a seal between the receptacle and the side of the patient's head.

4. Surgical apparatus as claimed in claim 1, in which the receptacle is provided with a drain tube for conducting away collected liquid.

5. Surgical apparatus as claimed in claim 4, in which a filter is arranged in the receptacle so that any solid matter in the liquid is retained on the filter when the liquid is drained away.

6. Surgical apparatus as claimed in claim 4, in which the drain tube is connected to a reservoir for collecting liquid drained out of the receptacle.

7. Surgical apparatus as claimed in claim 6, in which the reservoir comprises a flexible bag.

8. Surgical apparatus for use in carrying out syringing of a patient's ear and the caloric test of vestibular function, the apparatus comprising:
   (a) a rigid frame member;
   (b) a downwardly tapering flexible plastic bag;
   (c) means which releasably connect the bag to the rigid frame member with the bag suspended from the rigid frame member to form a receptacle with the rigid frame member defining the rim of the receptacle;
   (d) a first downwadly extending recess in one side of the receptacle defined by downwardly extending loop in the frame member, said first recess being shaped to receive the ear of a patient with the said one side of the receptacle extending up the side of the patient's head in front of and behind the ear;
   (e) a second downwardly extending recess in the opposite side of the bag, through which second recess a syringe can be inserted to pass across the receptacle and into the ear;
   (f) a resilient pad arranged on the said one side of the receptacle around the said first recess to form a seal with the side of the patient's head around the patient's ear;
   (g) an elastic strap connected to the receptacle for fitting around the patient's head to hold the receptacle in position and press the said resilient pad gently against the patient's head;
   (h) an outlet from the tapering flexible plastic bag at the lower end of the bag;
   (i) a filter arranged in the bag above the said outlet;
   (j) a plastic drain tube secured to the said outlet;
   (k) a reservoir for liquid, secured to the lower end of the drain tube, the reservoir being in the form of a second flexible plastic bag;
   (l) an outlet from said reservoir;
   (m) valve means controlling the outlet from said reservoir; and
   (n) means for attaching said reservoir to a support.

* * * * *